(12) United States Patent
Garcon-Johnson et al.

(10) Patent No.: US 6,893,644 B2
(45) Date of Patent: May 17, 2005

(54) HEPATITIS VACCINES CONTAINING 3-O-DEACYLATED MONOPHOSHORYL LIPID A

(75) Inventors: Nathalie Marie-Josephe Claude Garcon-Johnson, Wavre (BE); Pierre Hauser, Chaumont-Gistoux (BE); Clothilde Thiriart, Brussels (BE); Pierre Voet, Izel (BE)

(73) Assignee: SmithKline Beecham Biologicals s.a., Rixensart (BE)

( * ) Notice: Subject to any disclaimer, the term of this patent is extended or adjusted under 35 U.S.C. 154(b) by 0 days.

(21) Appl. No.: 10/465,763

(22) Filed: Jun. 19, 2003

(65) Prior Publication Data

US 2003/0211120 A1 Nov. 13, 2003

Related U.S. Application Data

(62) Division of application No. 09/933,930, filed on Aug. 21, 2001, now Pat. No. 6,620,414, which is a continuation of application No. 08/307,668, filed as application No. PCT/EP93/00712 on Mar. 24, 1993, now abandoned.

(30) Foreign Application Priority Data

| Mar. 27, 1992 | (GB) | 9206786 |
| Mar. 27, 1992 | (GB) | 9206788 |
| Mar. 27, 1992 | (GB) | 9206789 |
| Mar. 27, 1992 | (GB) | 9206797 |

(51) Int. Cl.$^7$ .................... A61K 45/00; A61K 47/44
(52) U.S. Cl. .................... 424/283.1; 424/184.1; 424/189.1; 424/204.1; 424/201.1; 424/225.1; 424/226.1; 424/227.1; 424/278.1
(58) Field of Search ............ 424/278.1, 283.1, 424/184.1, 189.1, 201.1, 202.1, 204.1, 225.1, 226.1, 227.1

(56) References Cited

U.S. PATENT DOCUMENTS

| 4,857,634 A | 8/1989 | Minor et al. .............. 530/324 |
| 4,912,094 A | 3/1990 | Myers et al. ............... 514/54 |
| 5,776,468 A | 7/1998 | Hauser et al. ............. 424/226.1 |
| 5,972,346 A | * 10/1999 | Hauser et al. ............. 424/227.1 |
| 6,372,227 B1 | 4/2002 | Garcon et al. ............. 424/184.1 |
| 6,488,934 B1 | * 12/2002 | Hauser et al. ............. 424/201.1 |
| 6,620,414 B2 | * 9/2003 | Garcon-Johnson et al. ...... 424/226.1 |

FOREIGN PATENT DOCUMENTS

| EP | 0 175 261 | 3/1986 |
| EP | 0 318 216 | 5/1989 |
| EP | 0 414 374 A2 | 2/1991 |
| EP | 0 419 182 A1 | 3/1991 |
| GB | 2 220 211 A | 6/1989 |
| GB | 2212511 A | 7/1989 |
| WO | WO 89/12462 | 12/1989 |
| WO | WO 91/16926 | 11/1991 |
| WO | WO 92/06113 | 4/1992 |
| WO | WO 92/11291 | 7/1992 |
| WO | WO 92/16231 | 10/1992 |
| WO | WO 98/16556 | 10/1992 |
| WO | WO 93/10152 | 5/1993 |

OTHER PUBLICATIONS

MAnnucci et al. Arch Intern Med 1989 vol. 149, pp. 1333–1337.*
Wagner et al. Clinical Investigation 1992 vol. 70, pp. 585–587.*
Coursaget, et a., "Simultaneous Administration of Diphtheria–Tetanus–Pertussis–Pollo and Hepatitis B Vaccines in a Simplified Immunization Program: Immune Response to Diphtheria Toxoid, Tetanus Toxoid, Pertussis, and Hepatitis B Surface Antigen", Infection and Immunity, 51: No. 3, pp. 784–787 (1986).
Myers, et al., " A Critical Determinant of Lipid A Endotoxic Activity", Cellular & Molecular Aspects of Endotoxin Reactions, pp. 145–156 (1990).
Jilg, et al., "Hepatitis A Vaccine", Vaccines, 2nd edition, pp. 583–595 (1994).
Johnson, et al., "Advances in Experimental Medicine and Biology", vol. 256 pp. 567–579 (1990).
Takayama, et al., "Adjuvant Activity of Non–Ionic Block Copolymers. V. Modulation of Antibody Isotype by Lipopolysaccharides, Lipid A and Precursors," Vaccine 9: 257–262 (1989).
Brynestad, et al., "Influence of Peptide Acylation, Liposome Incorporation, and Synthetic Immunomodulators on the Immunogenicity of a 1–23 Peptide of Glycoprotein D of Herpes Simplex Virus: Implications for Subunit Vaccines," J. Virol. 64 pp. 680–685 (1990).
Tsujimoto, et al., "Enhancement of Humoral Immune Responses Against Viral Vaccines by a Non–pyrogenic 6–0 Acyl–Muramyldipeptide ad synthetic low toxicity analogues of lipid A," Vaccine, 7: 39–48 (1989).
Richards, et al., "Immunogenicity of Liposomal Malaria Sporozoite Antigen in Monkeys: Adjuvant Effects of Aluminum Hydroxide and Non–Pyrogenic Liposomal Lipid A," Vaccine, 7, pp: 506–512 (1989).
Farci, et al., "Lack of Protective Immunity Against Reinfection with hepatitis C Virus," Science, 258: pp. 135–140 (1992).
Koff, RS, "A Redoubtable Obstacle to a Hepatitis C Vaccine," Gastroenterology, 104: pp. 1228–1229 (1993).

* cited by examiner

Primary Examiner—James Housel
Assistant Examiner—Myron G. Hill
(74) Attorney, Agent, or Firm—William R. Majarian; Stephen Ventianer; Charles M. Kinzig

(57) ABSTRACT

A vaccine formulation for the treatment or prophylaxis of hepatitis, especially hepatitis, especially hepatitis B, infections is provided comprising the hepatitis antigen and a suitable carrier such as alum in combination with 3-O-deacylated monophosphoryl lipid. A combination vaccines including the vaccine formulation are also described.

13 Claims, 1 Drawing Sheet

HEPATITIS VACCINES CONTAINING 3-O-DEACYLATED MONOPHOSHORYL LIPID A

CROSS REFERENCES TO RELATED APPLICATIONS

Figure 1:
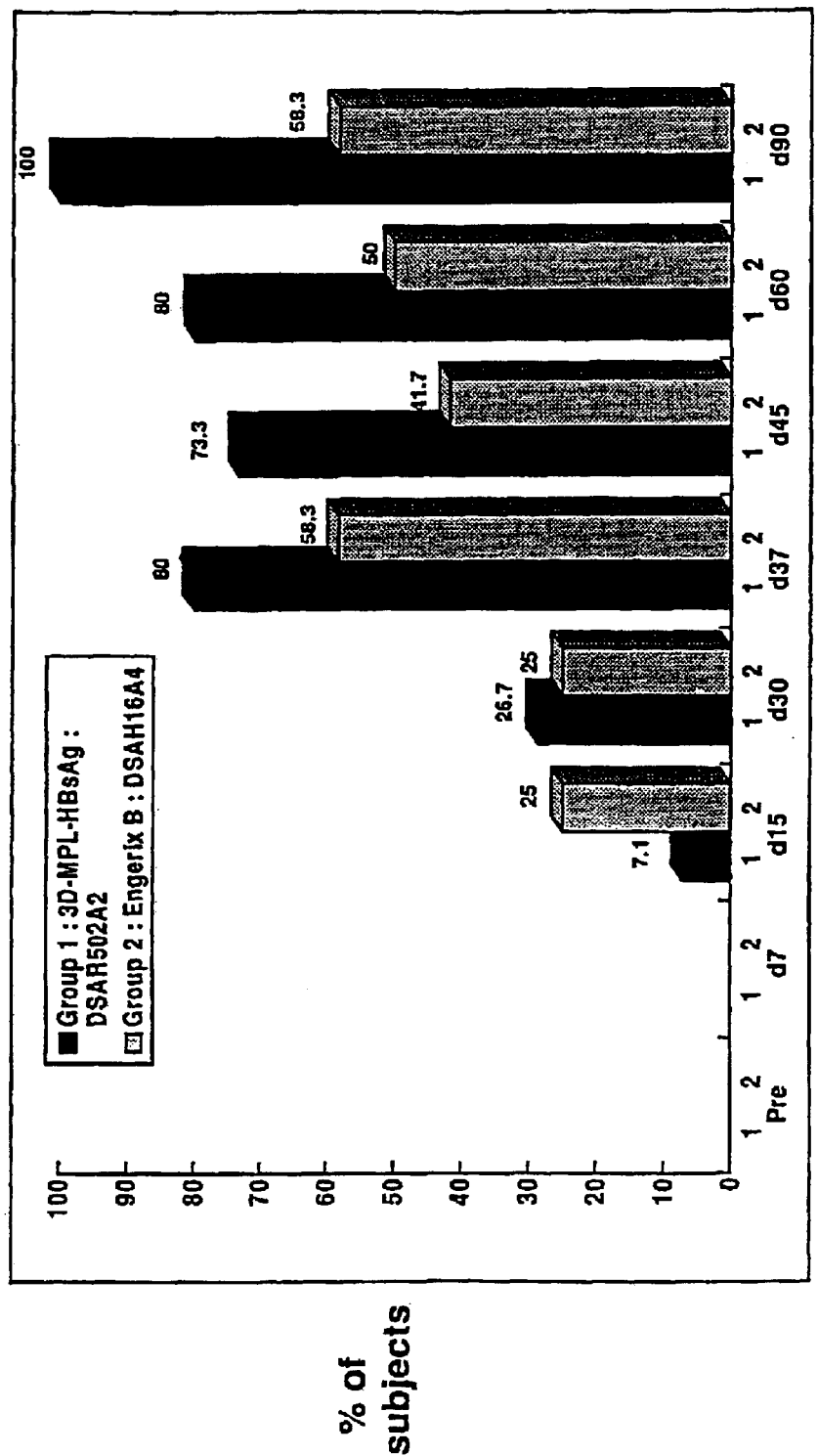

This application is a divisional of application Ser. No. 09/933,930, filed Aug. 21, 2001 (now U.S. Pat. No. 6,620, 414), which is a continuation of application Ser. No. 08/307, 668, (abandoned), filed Sep. 20, 1994, which is a U.S.C. 371 of International Application No. PCT/EP93/00712, filed Mar. 24, 1993, which claims priority of the following GB Application Nos. 9206786.7, filed Mar. 27, 1992, 9206788.3, filed Mar. 27, 1992, 9206789.1, filed Mar. 27, 1992, and 9206797.4, filed Mar. 27, 1992.

The present invention relates to novel vaccine formulations, methods for preparing them and to their use in therapy. In particular the present invention relates to novel formulations for treating Hepatitis infections and to combination vaccine formulations including a Hepatitis vaccine component.

Viral hepatitis, caused by the A, B, C, D, and E hepatitis viruses, is a very common viral illness. Via the B and C viruses, in particular, it is also responsible for many cases of liver cancer. Thus the development of effective vaccines is critical and, despite notable successes, is still an on-going task. A review on modern hepatitis vaccines, including a number of key references, may be found in the Lancet, May 12th 1990 at page 1142 ff (Prof A. L. W. F. Eddleston). See also 'Viral Hepatitis and Liver Disease' (Vyas, B. N., Dienstag, J. L., and Hoofnagle, J. L., eds, Grune and Stratton, Inc. (1984) and 'Viral Hepatitis and Liver Disease' (Proceedings of the 1990 International Symposium, eds F. B. Hollinger, S. M. Lemon and H. Margolis, published by Williams and Wilkins).

As used herein the expression 'hepatitis antigen' is used to refer to any antigenic material derived from a hepatitis virus which may be used to induce immunity to the virus in humans. The hepatitis antigen may be, for example, a polypeptide obtained by recombinant DNA techniques or an attenuated strain of hepatitis virus which has optionally been inactivated by known methods. The invention extends to all hepatitis antigens, whether A, B, C, D, or E, examples of which are discussed below.

Infection with hepatitis A virus (HAV) is a widespread problem but vaccines which can be used for mass immunisation are available, for example the product 'Havrix' (SmithKline Beecham Biologicals) which is a killed attenuated vaccine obtained from the HM-175 strain of HAV [see 'Inactivated Candidate Vaccines for Hepatitis A' by F. E. Andre, A Hepburn and E. D'Hondt, Prog Med. Virol. Vol 37, pages 72–95 (1990) and the product monograph 'Havrix' published by SmithKline Beecham Biologicals (1991)].

Flehmig et al (loc cit., pages 56–71) have reviewed the clinical aspects, virology, immunology and epidemiology of Hepatitis A and discussed approaches to the development of vaccines against this common viral infection.

As used herein the expression 'HAV antigen' refers to any antigen capable of stimulating neutralising antibody to HAV in humans. The HAV antigen may comprise live attenuated virus particles or inactivated attenuated virus particles or may be, for example an HAV capsid or HAV viral protein, which may conveniently be obtained by recombinant DNA technology.

Infection with hepatitis B virus (HBV) is a widespread problem but vaccines which can be used for mass immunisation are now available, for example the product 'Engerix-B' (SmithKline Beecham plc) which is obtained by genetic engineering techniques.

The preparation of Hepatitis B surface antigen (HBsAg) is well documented. See. for example, Harford et al in Develop. Biol. Standard 54, page 125 (1983), Gregg et al in Biotechnology, 5, page 479 (1987), EP-A-0 226 846, EP-A-0 299 108 and references therein.

As used herein the expression 'Hepatitis B surface antigen' or 'HBsAg' includes any HBsAg antigen or fragment thereof displaying the antigenicity of HBV surface antigen. It will be understood that in addition to the 226 amino acid sequence of the HBsAg S antigen (see Tiollais et al, Nature, 317, 489 (1985) and references therein) HBsAg as herein described may, if desired, contain all or part of a pre-S sequence as described in the above references and in EP-A-0 278 940. In particular the HBsAg may comprise a polypeptide comprising an amino acid sequence comprising residues 12–52 followed by residues 133–145 followed by residues 175–400 of the L-protein of HBsAg relative to the open reading frame on a Hepatitis B virus of ad serotype (this polypeptide is referred to as L*; see EP 0 414 374). HBsAg within the scope of the invention may also include the preS1-preS2-S polypeptide described in EP 0 198 474 (Endotronics) or analogues thereof such as those described in EP 0 304 578 (Mc Cormick and Jones). HBsAg as herein described can also refer to mutants, for example the 'escape mutant' described in WO 91/114703 or European Patent Application Publication Number 0 511 855 A1, especially HBsAg wherein the amino acid substitution at position 145 is to arginine from glycine.

Normally the HBsAg will be in particle form. The particles may comprise for example S protein alone or may be composite particles, for example (L*,S) where L* is as defined above and S denotes the S-protein of HBsAg. The said particle is advantageously in the form in which it is expressed in yeast.

Hepatitis C virus (HCV) is specifically discussed in GB 2 212 511B and references therein. It has been reported that vaccines may be prepared from one or more immunogenic polypeptides derived from HCV c DNA.

Hepatitis D virus is discussed in 'Viral Hepatitis and Liver Disease' (1990 Symposium (loc. cit.).

Hepatitis E virus (HEV) is specifically discussed in WO 89/12462 and references therein. An example of a vaccine composition includes, in a pharmacologically acceptable adjuvant, a recombinant protein or protein mixture derived from HEV.

Whilst experimental and commercially available Hepatitis vaccines, for example Havrix and Engerix-B, afford excellent results it is an accepted fact that an optimal vaccine needs to stimulate not only neutralising antibody but also needs to stimulate as effectively as possible cellular immunity mediated through T-cells. There also exists a need for combination vaccines containing a Hepatitis component to stimulate cellular immunity in this way. The present invention achieves these aims.

The present invention provides a vaccine comprising a hepatitis antigen in conjunction with 3-O-deacylated monophosphoryl lipid A (abbreviated herein to MPL) and a suitable carrier.

3-O-deacylated monophosphoryl lipid A (or 3 De-O-acylated monophosphoryl lipid A) has formerly been termed 3D-MPL or d3-MPL to indicate that position 3 of the reducing end glucosamine is de-O-acylated. For preparation, see GB 2 220 211 A Chemically it is a mixture of 3-deacylated monophosphoryl lipid A with 4, 5 or 6 acylated chains. Herein the term 3D-MPL (or d3-MPL) is abbreviated to MPL since 'MPL' is a Registered Trademark of Ribi Immunochem.,Montana which is used by Ribi to denote unambiguously their 3-O-deacylated monophosphoryl lipid A product.

GB 2 220 211A mentions that the endotoxicity of the previously used enterobacterial lipopolysacharides (LPS) is reduced while the immunogenic properties are conserved. However GB 2 220 211 cited these findings merely in connection with bacterial (Gram negative) systems. At the priority date of the present invention the suitability of 3-Deacylated monophosphoryl lipid A as an adjuvant for a vaccine containing a hepatitis viral antigen had not been suggested.

Surprisingly, however, it has been found that vaccine compositions according to the invention comprising hepatitis viral antigens have particularly advantageous properties as described herein.

A particular advantage is that the vaccine formulations of the invention are very effective in inducing protective immunity, even with very low doses of antigen.

They provide excellent protection against primary infection and stimulate advantageously both specific humoral (neutralising antibodies) and also effector cell mediated (DTH) immune responses.

A further important advantage is that vaccine compositions according to the invention may also be used as therapeutic vaccines.

The MPL as defined above will normally be present in the range of 10–100 ug, preferably 25–50 ug per dose wherein the Hepatitis antigen will be typically present in a range 2–50 ug per dose.

The carrier may be an oil in water emulsion, a lipid vehicle, or alum (aluminium salt).

Non-toxic oil in water emulsions preferably contain a non-toxic oil, e.g. squalene and an emulsifier such as Tween 80, in an aqueous carrier. The aqueous carrier may be, for example, phosphate buffered saline.

One embodiment of the invention is HAV antigen (for example as in Havrix) in admixture with MPL and aluminium hydroxide as described hereinbelow.

A further embodiment of the invention is HBsAg S antigen (for example as in Engerix-B) in admixture with MPL and aluminium hydroxide as described hereinbelow.

A further specific embodiment of the invention is HBsAg antigen as (L*,S) particles, defined hereinabove, in admixture with MPL and aluminium hydroxide.

In the above embodiments an oil in water emulsion may be used instead of alum.

Other embodiments arm given in the examples hereinbelow.

The invention in a further aspect provides a vaccine formulation as described herein for use in medical therapy, particularly for use in the treatment or prophylaxis of hepatitis viral infections. In a preferred aspect the vaccine according to the invention is a therapeutic vaccine useful for the treatment of ongoing hepatitis infections, more especially hepatitis B and/or hepatitis C infections in humans suffering therefrom.

In view of the surprisingly efficaceous results obtained, in a further preferred aspect the invention provides a vaccine composition for the treatment or prophylaxis of Hepatitis A and/or Hepatitis B infections.

Advantagously the hepatitis vaccine composition of the invention contains other antigens so that it is effective in the treatment or prophylaxis of one or more other bacterial, viral or fungal infections.

Accordingly the hepatitis vaccine formulation according to the invention preferably contains at least one other component selected from non-hepatitis antigens which are known in the art to afford protection against one or more of the following: diphtheria, tetanus, pertussis, *Haemophilus influenzae* b (Hib), and polio.

Preferably the vaccine according to the invention includes HBsAg as hereinabove defined.

Particular combination vaccines within the scope of the invention include a DTP (diphtheria-tetanus-pertussis)-hepatitis B combination vaccine formulation, an Hib-Hepatitis B vaccine formulation, a DYP-Hib-Hepatitis B vaccine formulation and an IPV (inactivated polio vaccine)-DTP-Hib-Hepatitis B vaccine formulation.

The above combinations may advantageously include a component which is protective against Hepatitis A, especially the killed attenuated strain derived from the HM-175 strain as is present in Havrix.

Suitable components for use in such vaccines are already commercially available and details may be obtained from the World Health Organisation. For example the IPV component may be the Salk inactivated polio vaccine. The pertussis vaccine may comprise whole cell or acellular product.

Advantageously the hepatitis or combination vaccine according to the invention is a paediatric vaccine.

Vaccine preparation is generally described in New Trends and Developments in Vaccines, edited by Voller et al., University Park Press, Baltimore, Md. U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of antigen in each vaccine dose is selected as an amount which induces an immunoprotective response without significant, adverse side effects in typical vaccinees. Such amount will vary depending on which specific immunogens are employed. Generally it is expected that each dose will comprise 1–1000 ug of total immunogen, preferably 2–100 ug, most preferably 4–40 ug. An optimal amount for a particular vaccine can be ascertained by standard studies involving observation of antibody titres and other responses in subjects. Following an initial vaccination, subjects may receive a boost in about 4 weeks.

In a further aspect of the present invention there is provided a method of manufacture of a vaccine effective in preventing or treating hepatitis infection, wherein the method comprises mixing the hepatitis antigen as defined herein with a carrier and MPL.

Using this method one or more additional components are preferably admixed with HBsAg to provide a combination vaccine, advantageously for paediatric use.

The following examples illustrate the invention and its advantages.

EXAMPLE 1

Hepatitis B Vaccine Formulation

MPL was obtained from Ribi Immunochem Research Inc. Aluminium hydroxide was obtained from Superfos (Alhydrogel).

MPL was resuspended in water for injection at a concentration varying from 0.2 to 1 mg/ml by sonication in a water bath until the particles reach a size of between 80 and 500 nm as measured by photo correlation light scattering.

1 to 20 ug of HBsAg (S-antigen as in Engerix B) in phosphate buffer solution at 1 mg/ml) is adsorbed on 30 to 100 ug of aluminium hydroxide (solution at 10.38 $Al^{3+}$ mg/ml) for one hour at room temperature under agitation. To the solution is then added 30 to 50 ug of DMPL (solution 1 mg/ml). Volume and osmolarity are adjusted to 600 ul with water for injection and phosphate buffer 5× concentrated. Solution is incubated at room temperature for 1 hour and kept at 4° C. until use. Maturation of the formulation occurs during storage. This represents 10 injecting doses for testing in mice.

A similar formulation may be prepared by using as the HBsAg component the composite (L*,S) antigen as defined hereinabove.

EXAMPLE 2

Hepatitis A Vaccine Formulation

MPL was obtained from Ribi Immunochem Research Inc. Aluminium hydroxide was obtained from Superfos (Alhydrogel).

HAV (360 to 22 EU per dose) is preadsorbed on 10% of the aluminium hydroxide final concentration (0.5 mg/ml). MPL (12.5 to 100 ug per dose) is added to the solution.

The remaining aluminium hydroxide is added to the solution and left for one hour at room temperature. Volumes are adjusted with phosphate buffer (phosphate 10 mM, NaCl 15 mM) and the final formulation is then stored at 4° C. until use.

EXAMPLE 3

Combination Vaccine Formulation—Hepatitis B+Hepatitis A

HBsAg is adsorbed on 90% of the final amount of aluminium hydroxide (0.5 mg/ml) and incubated overnight at room temperature. The pH is adjusted to 6.2 and the preparation is left 14 days at room temperature for maturation.

Hepatitis A antigen at 360 to 22 EU per dose, in the form of an inactivated derivative of the HM-175 strain (as in Havrix) is preadsorbed on 10% of the aluminium hydroxide final concentration (0.5 mg/ml). The remaining aluminium hydroxide is then added to the solution and left for one hour at room temperature under agitation.

The HAV adsorbed on aluminium hydroxide is then added to the HBsAg formulation.

MPL is added to the HAV/HBsAg solution at a final concentration of 12.5 to 100 ug per 1 ml dose, the volume is adjusted to the final dose volume, and the formulation is stored at 4° C. until used.

EXAMPLE 4

Combination Vaccines Containing Additional Antigens

Combination vaccines containing DTP, IPV, Hib or acellular or whole cell pertussis antigens are prepared by adding one or more of the desired antigens to the formulations described in Example 1, Example 2 or Example 3 above.

EXAMPLE 5

Increase of Humoral Immunity and Induction of Cell Mediated Immunity by Immunization of Mice with HBsAgFormulated with Aluminium Hydroxide and MPL A. Effect of Al(OH)3+MPL on Induction of Anti-HBs Antibodies Balb/c mice were immunized by the subcutaneous route or by the intradermal route with recombinant HBsAg adsorbed on Al(OH)3 with MPL as adjuvant. Mice were immunized twice with HBsAg/Al/MPL formulations and the antibody response was measured after the first and the second doses. Total Ig were measured by ELISA or AUSAB kit (Abbott Lab,. Ill.) and a particular attention was given to the induction of antibodies of the IgG2a isotype since this isotype is mainly induced by secretion of g-Interferon. The induction of this isotype thus indirectly reflects the activation of cell mediated immunity, namely the activation of Th1.

The ratio HBsAg/MPL has been investigated as well as the size of MPL particles since suspension of MPL in water can result in particles of <100 nm or >500 nm.

Experiment I—Effect of MPL (>500 nm) Dose on Immunogenicity of rec.HBsAg Adsorbed on Al(OH)3

Groups of 10 female Balb/c mice were injected by the subcutaneous route with 2.5 mcg of recHBsAg adsorbed on 50 mcg of Al+++ (as Al(OH)3) and increasing amounts of MPL (3.1 to 50 mcg) with a particle size of >500 nm. The mice were injected twice in a volume of 100 mcl and at 2 weeks interval. They were bled 2 weeks after the first injection (partial bleeding) and one week after the booster. Total anti-HBs IgG and specific IgG2a were measured by ELISA using recHBsAg as capture antigen. The titers were expressed as the reciprocal of the dilution corresponding to 50% of the maximal value (mid-point dilution). The results are given at table 1. They indicate an increase of both specific IgG and IgG2a with increasing doses of MPL, particularly for doses of 12.5 to 50 mcg. The effect is seen for both primary and secondary responses and is particularly obvious for IgG2a (up to 20 fold increase) indirectly indicating a secretion of g-interferon induced by the immunization with MPL.

Experiment II—Comparison of Clinical Lots of Adsorbed recHBsAg Containing or not Containing MPL (>500 nm)

3 clinical lots of recHBsAg adsorbed on Al(OH)3 were prepared: lot DSAH16 contained no MPL and served as control. Lots DSAR501 and 502 were prepared in a similar way (20 mcg of recHBsAg adsorbed on 0.5 mg Al+++ as Al(OH)3) but contained 50 mcg of MPL (>500 nm).

The 3 lots were injected subcutaneously to groups of 10 mice (200 mcl containing 2.5 mcg HBsAg, 100 mcg Al+++ and 6.25 mcg MPL), twice at 2 weeks interval. The mice were bled at day 14 and 1 week after the booster. Anti-HBs antibodies were measured using AUSAB kit or an in-house ELISA for either IgG or IgG2a. The results are given in table 2. They indicate that, 2 weeks after the first injection, the 2 lots containing MPL induce a very significant anti-HBs response (12.4 and 41.9 mIU/ml) while the lot which does not contain MPL only induces a marginal response (0.75 mIU/ml). The number of responders is also higher with MPL (9/10 and 9/10 versus 1/10 in absence of MPL). The effect of MPL is confirmed after the booster since the titers obtained for lots DSAR501 and 502 are about 6 fold higher than that observed without MPL.

This indicates that, at least in mice, MPL (>500 nm) can improve both the kinetics of the anti-HBs response and the level of the anti-HBs response.

These results were confirmed when specific IgG and IgG2a are measured after immunization with lots DSAH16 (without MPL) and DSAR502 (with MPL): the anti-HBs IgG titer is 5 (primary response) and 3 (secondary response) times higher when MPL is present.

For the IgG2a response, the effect of MPL is even more striking, at least after the second dose, indicating a preferential induction of IgG2a. This indirectly reflects activation of cell-mediated immunity (secretion of g-interferon) by the preparation containing MPL.

Experiment III—Effect of MPL (<100 nm) Dose on Immunogenicity of recHBsAg Adsorbed on Al(OH)3

Because MPL is much easier to obtain in a reproducible way as <100 nm than as > 500 nm particles, the effect of <100 nm MPL particles on the immunogenicity of recHBsAg previously adsorbed on Al(OH)3 was investigated.

Groups of 10 mice (Balb/c, female, 7 weeks old) were injected subcutaneously with 1 mcg of recHBsAg adsorbed on 50 mcg of Al+++ (as Al(OH)3) and in presence of increasing amounts (3.1 to 25 mcg) of MPL(<100 nm). The mice were injected twice at 2 weeks interval with a volume of 200 mcl. They were bled 2 weeks after the first injection and 1 week after the booster. The anti-HBs response was evaluated by ELISA (total Ig, IgG, IgG2a) on pooled sera. The titers were expressed as mid-point dilutions (reciprocal of the dilution giving 50% of the highest values). The results indicate that as few as 3.1 mcg of MPL induce a strong increase of the antibody response both for primary and secondary responses. The response culminates for 6.25 mcg and decreases afterwards to become similar to that found without MPL when high doses of MPL (25 mcg) are used The pattern of the antibody response is similar for IgG, IgG2a and total Ig. It contrasts with results obtained for MPL of higher size (>500 nm) (see experiment I) and suggests that small size (<100 nm) particles of MPL are more effective than larger size (>500 nm) particles (at least for humoral immunity), since less MPL is needed to obtain the maximal effect. The highest activity of small size MPL was confirmed in several experiments.

As shown for larger size MP (>500 nm), the adjuvant effect of MPL is higher for IgG2 than for total IgG or Ig. At the maximal effect of the secondary response (6.25 mcg of MPL), there is a 25 fold increase for IgG2a while the increase for IgG or total Ig was 7.6 and 4.3 respectively.

B. Induction of Cell-Mediated Immunity by recHBsAg Adsorbed on Al(OH)3-Effect of MPL If humoral immunity is sufficient to protect against Hepatitis B, the induction of cell-mediated immunity (CTL, Th1) could be of particular importance for the treatment of the disease.

New formulations are required however for therapeutic vaccines since Al(OH)3 is capable of improving humoral immunity but not cell mediated immunity.

We have investigated the effect of MPL on the induction of Th1 cells capable of secreting IL-2 and g-(i.e. gamma) interferon in Balb/c mice immunized with recHBsAg adsorbed on Al(OH)3.

Experiment I—Effect of MPL (>500 nm) on Induction of Th1 Cells after Immunization of Balb/c Mice with Al(OH)3 Adsorbed HBsAg A group of 10 Balb/c mice (female, 5 weeks old) were immunized by injection in each footpad of 30 mcl containing 10 mcg of HBsAg, 15 mcg of Al+++ (as Al(OH)3) and 15 mcg of MPL. Control mice were injected similarly with the same amount of recHBsAg either mixed with FCA (positive control) or adsorbed on Al(OH)3 without MPL (negative control).

Six days after the immunization, the mice were killed and the popliteal lymph nodes were removed. The lymph node cells (LNC 2.105/ml) were cultivated for different periods of time (24 hrs to 74 hrs) in RPMI medium supplemented with 1% of negative mouse serum and containing 5 mcg/ml of recHBsAg. After termination of the culture, the amount of IL-2, INF-g and IL-4 secreted in the medium was measured. IL-2 was estimated by its ability to stimulate the proliferation (evaluated by incorporation of 3H-Thymidine) of an IL-2-dependent CTL line (VDA2 cells) and the titer was expressed as stimulation index (SI=amount of 3H-Thymidine incorporated in stimulated cells/amount of 3H-Thymidine incorporated in non stimulated cells). The amount of IL-4 and INF-g was measured using commercial ELISA kits (Holland Biotechnology for IFN-g and Endogen for IL-4). The titers were expressed in pg of IFN-g/ml.

The results indicate that no significant amount of IL-2, IL-4 or INF-g is secreted by LNC from mice immunized with HBsAg adsorbed on Al(OH)3. On the contrary, high levels of IL-2 (I.S.=38 at 48 hrs) and a significant amount of INF-g are secreted by LNC from mice immunized with HBsAg adsorbed on Al(OH)3 +MPL. This secretion is similar (INF-g) or higher (IL-2) to that observed for mice immunized with HBsAg+FCA and the in vitro secretion occurs earlier.

No IL-4 was detected after immunization with HBsAg adsorbed on Al(OH)3 even in presence of MPL.

This secretion profile indicates that specific Th1 cells (IL-2, INF-g) have been induced by immunization with adsorbed HBsAg in presence of MPL but not in absence of MPL. However, no Th2 (IL-4) were detected in these conditions of immunization.

Experiment II—Effect of the Dose of MPL (<100 nm) on the Induction of Th1 Cells after Immunization of Balb/c Mice with Al(OH)3 Adsorbed recHBsAg Groups of 5 Balb/c mice were immunized in each of the 2 footpads with 30 mcl containing 10 mcg of recHBsAg adsorbed on 15 mcg of Al+++ (as Al(OH)3) and with increasing amounts of MPL (100 nm, 0 to 15 mcg).

Six days after the injection, the mice were killed and the popliteal lymph node cells (LNC) were cultivated at 2.106 cells/ml in RPMI supplemented with 1% negative mouse serum for different periods of time (24 hrs to 96/25) in presence of 5 mcg/ml of recHBsAg.

The secretion of IL-2 was measured by stimulation of the proliferation of VDA2 cells and concentration of IL-2 is expressed as Stimulation Index (SI); the secretion of INF-g was measured using a commercial kit and expressed in pg/ml.

It was found that the secretion of IL-2 is dramatically increased by the lower dose of MPL (7.5 mcg) and a maximal effect is obtained for 15 mcg of MPL.

The secretion of IL-2 is generally more important at 24 hrs than at 48 or 72 hrs.

The secretion of INF-g is absent when HBsAg is adsorbed on Al(OH)3 in absence of MPL. A small dose (7.5 mcg) of MPL induces a secretion of INF-g and again, the maximal effect is obtained for 15 mcg of MPL. Contrary to what is observed for IL-2, the secretion of INF-g is delayed in the culture and increases with time up to 96 hours.

Taken together these data indicate that MPL (100 nm) is a potent inducer of Th1 when combined with HBsAg adsorbed on Al(OH)3.

C. Conclusion

The effect of a formulation containing HBsAg adsorbed on Al(OH)3 and MPL on the induction of both humoral and cell-mediate immunity in Balb/c mice has been investigated. The results indicate that MPL clearly improves the kinetics of the anti-HBs response since much more anti-HBs antibodies are found after both the primary and secondary immunizations. The quality of the anti-HBs is also modified and a preferential induction of IgG2a has been observed, reflecting indirectly secretion of INF-g and thus induction of a cell-mediated immunity.

Direct evaluation of the induction of Th1 cells by formulations containing HBsAg, Al(OH)3 and MPL-clearly indicates that MPL is a potent inducer of Th1 cells secreting both IL-2 and INF-g. This kind of formulation is thus important in the development of therapeutic vaccines.

For Tables showing the results of experiments described above, see Tables 1 to 6 below.

EXAMPLE 6

Clinical Use of MPL as Adjuvant to HBsAg—Preliminary Results

Study MPL-HBV-002 (Ongoing)

This study compares HBsAg-MPL to Engerix-B in young healthy unprimed adult volunteers.

End points

Immunogenicity: magnitude of anti-HBs antibodies response

Kinetics of anti-HBs antibody response

Cell-mediated immunity induced by both vaccines (in vitro and in vivo).

Reactogenicity, toxicology and safety.

Material and Methods a) Vaccines

|    | HBsAg (as in Engerix B) | Alum      | MPL     |
|----|-------------------------|-----------|---------|
| I  | 20 µg                   | 500 µg    | 50 µg   |
| II | 20 µg                   | 500 µg    | None    | b) Population

Healthy adult volunteers, between 18 and 30 years of age. They must be negative for HBV markers and must never have been vaccinated against hepatitis B.

c) Design

Double-blind, randomized study.

Schedule of vaccination: 0,1,6 months

Follow-up till month 12.

Blood sampling:

Anti-HBs antibody testing is done before, 7 days, 15 days, 30 days after each vaccination.

Biochemistry and haematology parameters are evaluated before and 2 days after each dose.

Blood for evaluation of the cell-mediated immunity is taken before and after the primary vaccination course and the booster dose.

Reactogenicity:

The subjects are required to record occurrence of local and general signs and symptoms on diary cards on the day of vaccination and during the 7 following days.

Results

The results up to 2 months after the second dose are given below.

Population:

A total of 29 subjects have given their informed consent but only 27—15 male and 12 female—met the entry criteria. 15 subjects were allocated to Group I and 12 to Group II. The mean age was 22 years.

Safety:

No serious adverse experience was reported and no subjects were withdrawn or had to be withdrawn from the study. No clinically significant modification of the haematological or biochemical parameters were observed. The incidence and severity of local and general signs and symptoms is similar in both vaccine groups.

Immunogenicity:

The anti-HBs antibody titres have been measured up to day 90, ie 2 months after the second dose. The seroconversion rate (SC, in %) is defined as the appearance of antibodies in initially seronegative subjects.

The seroprotection rate is defined as the percentage of subjects with protective anti-HBs antibody titres. If there seems to be no clear difference in the magnitude of the antibody response with GMTs comparable between the two groups, the kinetics of the response is different and there is a clear advantage of the vaccine containing MPL. Indeed, 7 days after the second dose, 93% and 80% of the subjects receiving the MPL-HBV vaccine seroconverted and were protected respectively in comparison with a seroconversion rate of 95% and a seroprotection rate of 58% in the Engerix-B group. This difference is maintained up to two months after the second dose and is particularly evident for the seroprotection rate. At this time point, all subjects who received the MPL-HBV vaccine are protected in comparison with 58% of the subjects vaccinated with the alum adjuvanted vaccine.

Study MPL—HBV-003 (Ongoing)

The material and methods are similar to those of MPL-HBV002 study (see above). The schedules of vaccination are different:

| Group | No of subjects | Vaccine         | Schedule   |
|-------|----------------|-----------------|------------|
| I     | 25             | MPL-HBsAg/alum  | 0–2 months |
| II    | 25             | Engerix-B       | 0–2 months |
| III   | 25             | MPL-HBsAg/alum  | 0–6 months |
| IV    | 25             | Engerix-B       | 0–6 months |

Results

Although the kinetics of the anti-HBs antibody response has not been followed as closely as in the previous study, it appears that the same conclusion can be drawn in the present study. The subjects who receive the MPL adjuvanted vaccine respond better after the second dose than those injected with the vaccine without MPL. All but one subject (95.8%) have protective titres one month after the second dose of MPL-HBV vaccine, as compared with 72.7% in the Engerix-B group. Furthermore, in contrast with the previous trial, the MPL-BBV vaccine seems to induce higher antibody titres than Engerix-B (214 and 72 mIU/ml, respectively) indicating that a longer interval between the doses is perhaps important.

Conclusions

In these two studies, the hepatitis B vaccine (containing HBsAg as in Engerix B and alum) adjuvanted with MPL was evaluated in healthy adult volunteers and compared to Engerix-B (HBsAg S-antigen formulated with alum) according to various schedules. If there seems to be no difference in immunogenicity between the two vaccines after one dose, the MPL-HBV vaccine shows a clear advantage after the second dose, especially with a much higher percentage of subjects with protective antibody titres. The GMTs are also higher in this group when the two doses are given at two months interval instead of one month.

This could indicate a better priming of the response when MPL is added to the antigen. Such a vaccine would therefore be of great value in slow or low responders to hepatitis B vaccination, such as older people or immunocompromised subjects.

For Tables and a FIGURE showing the results of the experiments described above, see Tables 7 and 8 below and FIG 1.

EXAMPLE 7
Hepatitis A—MPL Study in Mice

The following experiment demonstrates that addition of MPL to Hepatitis A vaccine has a beneficial effect: This is reflected in a lower ED50-value (dose, expressed in ELISA units -EU-, that gives a serological response in 50% of the animals injected).

Method

NMRI mice were injected with 1 dose of experimental HAV vaccine containing 360-120-40-13.3 EU/dose combined with different concentrations of MPL (0-1.5-6-12.5 μg/dose). Blood samples were taken 28 days after inoculation and the serum tested in the HAVAB test (using a 20% cutoff). The ED50 (expressed in EU) was calculated and corresponds to the dose that induces a serological response in 50% of the animals tested.

RESULTS

Results are summarized in the following Table. The vaccine containing no MPL had an ED50 of 123.7 EU, whereas the vaccine containing 1.5 μg MPL/dose had an ED50 of 154. Higher doses of MPL had a beneficial affect (the ED50 was observed at lower EU values). At 12.5 μg MPL/dose, the ED50 observed was 47.1 EU.

Conclusion

The combination of the appropriate amount of MPL to HAV-vaccine improves the performance of this vaccine when tested in the mouse potency assay. 0–6 months

TABLE

Effect of the addition of MPL to Hepatitis A vaccine

| Dose of MPL added to HAV-vaccine (μg/dose) | ED50 (in EU/dose) |
|---|---|
| 0 | 123.7 |
| 1.5 | 154 |
| 6 | 101.1 |
| 12.5 | 47.1 |

TABLE 1

EFFECT OF INCREASING DOSES OF MPL (>500 NM) ON IMMUNOGENICITY OF RECHBSAG ADSORBED ON AL(OH)$_3$

| Amount of MPL | Anti-HBs response | | | |
|---|---|---|---|---|
| | Total IgG | | IgG2a | |
| (mcg/dose) | Day 14 | Day 21 | Day 14 | Day 21 |
| 0* | 69 | 743 | 3.2 | 11 |
| 3.13 | 122 | 541 | 3.8 | 20 |
| 6.25 | 296 | 882 | 6.4 | 24 |
| 12.5 | 371 | 1359 | 10 | 48 |

TABLE 1-continued

EFFECT OF INCREASING DOSES OF MPL (>500 NM) ON IMMUNOGENICITY OF RECHBSAG ADSORBED ON AL(OH)$_3$

| Amount of MPL | Anti-HBs response | | | |
|---|---|---|---|---|
| | Total IgG | | IgG2a | |
| (mcg/dose) | Day 14 | Day 21 | Day 14 | Day 21 |
| 25 | 456 | 1493 | 18 | 138 |
| 50 | 403 | 1776 | 33 | 242 |

*HBsAg on Al

TABLE 2

COMPARISON OF 3 CLINICAL LOTS CONTAINING OR NOT MPL AUSAB RESPONSE

| Lot | Dose of HBsAg on Al(OH)$_3$ (mcg) | Dose of MPL (mcg) | GMT Anti-HBs (mIU/ml) | |
|---|---|---|---|---|
| DSAH16 | 2.5 | 0 | 0.75 | 15.1 |
| DSAR501 | 2.5 | 6.25 | 12.4 | 96.7 |
| DSAR502 | 2.5 | 6.25 | 41.9 | 89.2 |

TABLE 3

COMPARISON OF 2 CLINICAL LOTS CONTAINING OR NOT MPL (>500 NM) ANTI-HBs IGG AND IGG2A RESPONSE

| Lot | Dose of HBsAg on Al(OH)$_3$ (mcg) | Dose of MPL (mcg) | Anti-HBs response | | | |
|---|---|---|---|---|---|---|
| | | | IgG | | IgG2a | |
| | | | d15 | d21 | d15 | d21 |
| DSAH16 | 2.5 | 0 | 20 | 178 | <5 | 5 |
| DSAR502 | 2.5 | 6.25 | 113 | 641 | <5 | 28 |

TABLE 4

EFFECT OF MPL (<100 NM) DOSE ON IMMUNOGENICITY Of RECHBsAG ADSORBED ON AL(OH)$_3$

| Dose of HBsAg on Al(OH)$_3$ (mcg) | Dose oMPLf (<100 nm) (mcg) | Anti-HBs response | | | | | |
|---|---|---|---|---|---|---|---|
| | | Total Ig | | IgG | | IgG2a | |
| | | d15 | d21 | d15 | d21 | d15 | d21 |
| 1 | 0 | 30 | 637 | 67 | 516 | 15 | 99 |
| 1 | 3.12 | 312 | 2302 | 335 | 3532 | 167 | 1752 |
| 1 | 6.25 | 538 | 2719 | 856 | 3932 | 261 | 2521 |
| 1 | 12.5 | 396 | 2104 | 485 | 3625 | 125 | 1393 |
| 1 | 25.0 | 38 | 446 | 141 | 638 | 28 | 233 |

TABLE 5

EFFECT OF MPL (>500 NM) ON THE INDUCTION OF HBSAC SPECIFIC TH1 CELLS IN BALB/C MICE

| Dose of HBsAg (mcg/mouse) | Formulation | IL-2 (Sl) 24 h | 48 h | 72 h | INF-γ (pg/ml) 24 h | 48 h | 72 h | IL-4 (pg/ml) 24 h | 48 h | 72 h |
|---|---|---|---|---|---|---|---|---|---|---|
| 20 | FCA | 1.3 | 2.0 | 8.0 | <125 | <125 | 385 | NT | NT | NT |
| — | FCA | 0.7 | 1.8 | 0.7 | <125 | <125 | <125 | NT | NT | NT |
| 20 | Al(OH)$_3$ | 1.0 | 1.4 | 1.2 | <125 | <125 | <125 | <40 | <40 | <40 |
| 20 | Al(OH)$_3$ + MPL 30 mcg) | 2 | 38 | 10 | <125 | 280 | 280 | <40 | <40 | <40 |

After immunization as described in the text, lymph node cells were cultured with 5 mcg recHBsAg/ml for the indicated periods of time and the secretion of IL-2, INFγ- and IL-4 were measured using respectively VDA$_2$ T-cell line and 2 commercial ELISA kits.

TABLE 6

EFFECT OF DIFFERENT DOSES OF MPL (<100 NM) ON THE INDUCTION OF HBsAC SPECIFIC TH1 CELLS

| Dose of HBsAg (mcg/mouse) | Formu-lation | IL-2 (Sl) 24 h | 48 h | 72 h | INF-γ (pg/ml) 24 h | 48 h | 72 h | 96 h |
|---|---|---|---|---|---|---|---|---|
| 20 | 0 | 2.6 | 28 | 21.8 | <67 | <67 | <67 | <67 |
| 20 | 7.5 | 207 | 173 | 58 | <67 | 207 | 522 | 698 |
| 20 | 15 | 270 | 71 | 36 | 275 | 878 | 1249 | 1582 |
| 20 | 30 | 41 | 59 | 36 | <67 | <67 | <67 | 207 |

TABLE 7

MPL-HBV-002

| GROUP | VACCINE | TIMING | N | SEROCONVERSION RATE (%) | GMT | SEROPROTECTION RATE (%) |
|---|---|---|---|---|---|---|
| I | MPL-HBsAg (20 μg) | Pre | 15 | 0.0 | 0 | 0.0 |
| | | Pl (d7) | 15 | 0.0 | | 0.0 |
| | | Pl (d15) | 14 | 42.9 | 4 | 7.1 |
| | | Pl (d30) | 15 | 40.0 | 13 | 26.7 |
| | | Pll (d37) | 15 | 93.3 | 41 | 80.0 |
| | | Pll (d45) | 15 | 100.0 | 42 | 73.3 |
| | | Pll (d60) | 15 | 100.0 | 25 | 80.0 |
| | | Pll (d90) | 15 | 100.0 | 44 | 100.0 |
| II | Engerix B (20 μg) | Pre | 12 | 0.0 | 0 | 0.0 |
| | | Pl (d7) | 12 | 0.0 | | 0.0 |
| | | Pl (d15) | 12 | 33.3 | 26 | 25.0 |
| | | Pl (d30) | 12 | 50.0 | 9 | 25.0 |
| | | Pll (d37) | 12 | 75.0 | 37 | 58.3 |
| | | Pll (d45) | 12 | 83.3 | 20 | 41.7 |
| | | Pll (d60) | 12 | 66.7 | 36 | 50.0 |
| | | Pll (d90) | 12 | 83.3 | 31 | 58.3 |

TABLE 8

MPL-HBV-003 STUDY

| Group | Vaccine | Timing | N | SC (%) | GMT | SP (%) |
|---|---|---|---|---|---|---|
| I | MPL-HBsAg (20 μg) | Pre | 25 | 0.0 | 0 | 0.0 |
| | | P1 (m1) | 23 | 56.5 | 10 | 26.1 |
| | | P1 (m2) | 24 | 66.7 | 6 | 16.7 |
| | | P2 (m3) | 24 | 100.0 | 214 | 95.8 |
| II | Engerix-B (20 μg) | Pre | 25 | 0.0 | 0 | 0.0 |
| | | P1 (m1) | 24 | 41.7 | 12 | 29.2 |
| | | P1 (m2) | 19 | 52.6 | 4 | 5.3 |
| | | P2 (m3) | 22 | 90.9 | 72 | 72.7 |

What is claimed is:

1. A method of treating a human subject suffering from or susceptible to hepatitis infections, the subject being an elderly or immunocompromised subject, the method comprising administering a vaccine composition, said composition comprising a viral hepatitis antigen selected from the group consisting of: a killed attenuated Hepatitis A virus, a Hepatitis B antigen, and a combination of a killed attenuated Hepatitis A virus—Hepatitis B antigen, in conjunction with 3-O-deacylated monophoshoryl lipid A and a suitable carrier, wherein said carrier is selected from the group consisting of: an aluminium salt and an oil water emulsion.

2. The method of claim 1 wherein the killed, attenuated Hepatitis A virus is the HM-175 strain of Hepatitis A virus.

3. The method of claim 1 wherein the viral hepatitis antigen is obtained from a Hepatitis B virus.

4. The method of claim 3 wherein the viral hepatitis antigen comprises Hepatitis B surface antigen (HBsAg) of a variant thereof.

5. The method of claim 4 wherein the HBsAg comprises the 226 amino acid-S antigen of HBsAg.

6. The method of claim 5 wherein the HBsAg further comprises a pre-S sequence.

7. The method of claim 5 wherein the HBsAg is the composite particle of the formula (L*, S) wherein L* denotes a modified L protein of Hepatitis B virus having an amino acid sequence comprising residues 12–52 followed by residues 133–145 followed by residues 175–400 of the L protein and S denotes the S-protein of HBsAg.

8. The method of claim 6 wherein the HBsAg is the composite particle of the formula (L*, S) wherein L* denotes a modified L protein of Hepatitis B virus having an amino acid sequence comprising residues 12–52 followed by residues 133–145 followed by residues 175–400 of the L protein and S denotes the S-protein of HBsAg.

9. The method of claim 3 wherein the vaccine composition further comprises a Hepatitis A antigen obtained from a killed attenuated Hepatitis A virus.

10. The method of claim 1 wherein the vaccine composition further comprises at least one other component selected from non-hepatitis antigens affording protection to one or more of diphtheria, tetanus, pertussis, *Haemophilus influenzae* b (Hib), and polio.

11. The method of claim 10 wherein the vaccine composition is a member selected from the group consisting of a DTP (dipthena-tetnus-pertussis)-HBsAg combination, an Hib-HBsAg combination, a DTP-Hib-HBsAg combination, and an IPV (inactivate polio vaccine)-DTP-Hib-HBsAg combination.

12. The method of claim 1 wherein the 3-O-deacylated monophoshoryl lipid A is present in the range of 10 ug–100 ug per dose.

13. The method of claim 1 wherein the aluminium salt is aluminium hydroxide.

* * * * *